United States Patent [19]

Engelhardt et al.

[11] Patent Number: 6,150,477
[45] Date of Patent: Nov. 21, 2000

[54] PROCESS FOR THE PREPARATION OF HYDROPHILIC HYDROGELS OF HIGH SWELLING CAPACITY

[75] Inventors: Fritz Engelhardt, Chesapeake, Va.; Manfred Mayer, Niedernhausen; Uwe Nickel, Bad Homburg, both of Germany

[73] Assignee: Hoechst Aktiengesellschaft, Germany

[21] Appl. No.: 08/880,228

[22] Filed: Jun. 23, 1997

[30] Foreign Application Priority Data

Jun. 24, 1996 [DE] Germany .......................... 196 25 143

[51] Int. Cl.$^7$ .............................. C08F 2/00; C08F 20/54; C08F 20/10; B01J 8/18
[52] U.S. Cl. ..................... 526/88; 526/317.1; 526/303.1; 526/319; 422/139
[58] Field of Search .................................. 526/88, 317.1, 526/303.1, 319; 422/139

[56] References Cited

U.S. PATENT DOCUMENTS

| | | | |
|---|---|---|---|
| 3,723,395 | 3/1973 | Warzell | 526/65 |
| 4,582,224 | 4/1986 | Proksa et al. | 222/135 |
| 5,026,800 | 6/1991 | Kimura et al. | 526/200 |
| 5,034,196 | 7/1991 | Zenz et al. | 422/142 |
| 5,059,664 | 10/1991 | Yada et al. | 526/240 |
| 5,139,762 | 8/1992 | Flagella | 423/349 |
| 5,244,735 | 9/1993 | Kimura et al. | 428/402 |
| 5,338,810 | 8/1994 | Shimomura et al. | 526/75 |
| 5,389,722 | 2/1995 | Nagasuna et al. | 525/55 |
| 5,447,727 | 9/1995 | Graham | 424/487 |
| 5,506,324 | 4/1996 | Gartner et al. | 526/318.41 |
| 5,788,932 | 8/1998 | Proksa et al. | 422/133 |

FOREIGN PATENT DOCUMENTS 348180  12/1989  European Pat. Off.

*Primary Examiner*—David W. Wu
*Assistant Examiner*—Tanya Zalukaeva
*Attorney, Agent, or Firm*—Connolly Bove Lodge & Hutz

[57] ABSTRACT

The present invention relates to a process for the preparation of hydrophilic hydrogels of high swelling capacity by (co)polymerization of hydrophilic monomers in a fluidized bed apparatus.

14 Claims, 1 Drawing Sheet

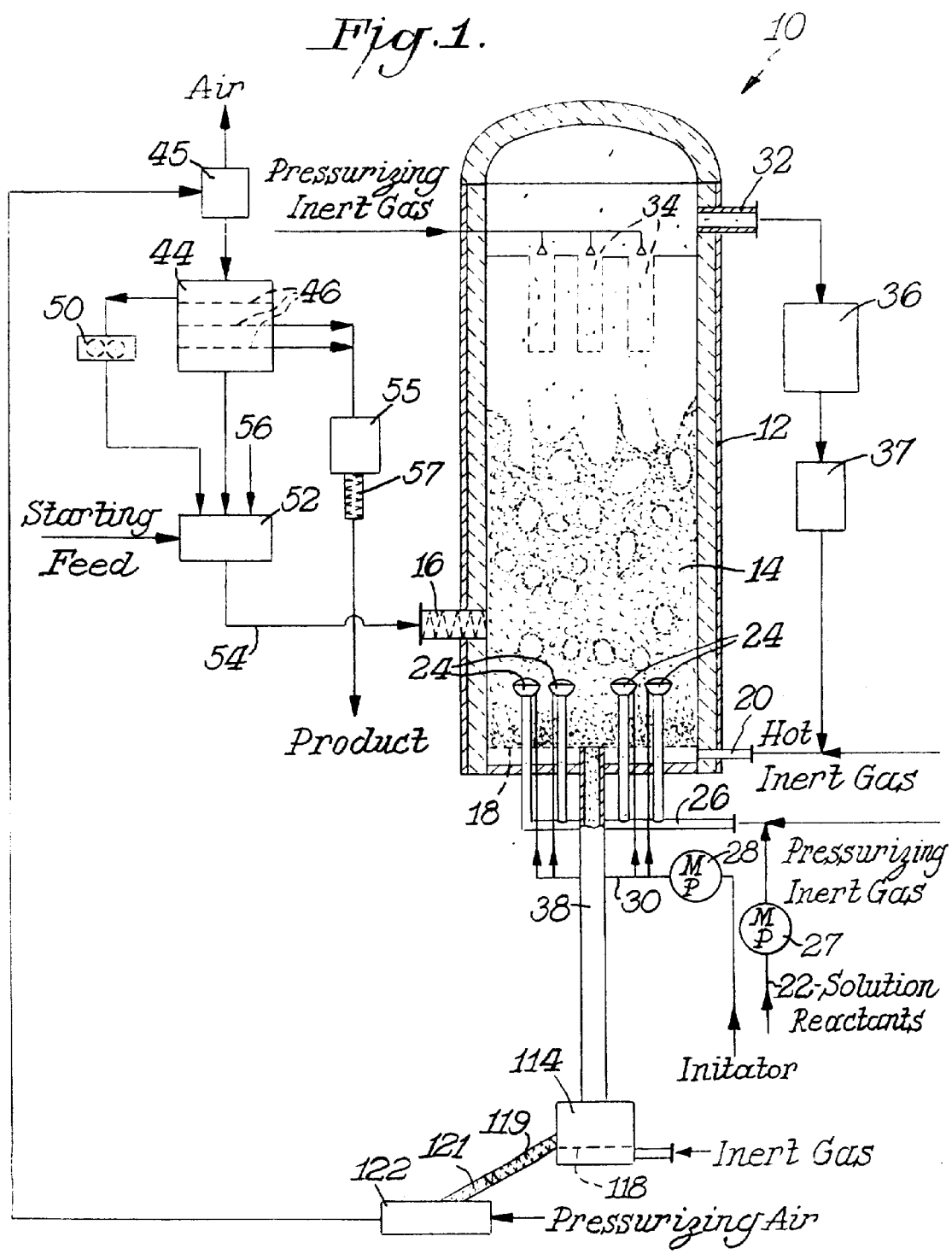
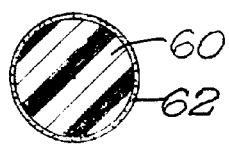

PROCESS FOR THE PREPARATION OF HYDROPHILIC HYDROGELS OF HIGH SWELLING CAPACITY

The present invention relates to a process for the preparation of hydrophilic hydrogels of high swelling capacity by (co)polymerization of hydrophilic monomers in a fluidized bed apparatus.

DESCRIPTION OF THE PRIOR ART

Hydrophilic hydrogels of high swelling capacity are, for example, polymers of (co)polymerized hydrophilic monomers. Such hydrogels are used as products which absorb aqueous solutions for the production of diapers, tampons, sanitary towels and other hygiene articles, and also as water-retaining agents in agriculture and horticulture.

Processes are known for the preparation of such hydrogels in which monomers, such as, for example, acrylic acid and methacrylic acid, are polymerized in aqueous solution, in acid form or neutralized to a certain percentage, with the addition of catalysts, initiators and crosslinking agents. The reaction solution is diluted with water here to the extent that a gel forms after the reaction. The dilution with water is carried out on the one hand to limit the maximum temperature which occurs due to heating as a result of the heat of polymerization, and on the other hand the processability of the gel to granules imposes limits on the solids content. The reaction is as a rule carried out with heating either in the static state (pot reactor or belt reactor) or in apparatuses with rotors, the reaction mass in each case being mixed and kneaded up to the gel phase. EP-B 223 063 discloses a process for the continuous preparation of crosslinked finely divided polymers in gel form in which pre-neutralized acrylic acid is reacted with comonomers in aqueous solution in a continuously operating single-shaft, cylindrical kneader at 45–80° C. and lumps of gel with a residual moisture content of 30 to 70% are discharged at the end. A disadvantage of this process is further processing of the viscous gel with expensive drying, comminution and sieving to the desired particle size. Dust and undesirable fine contents must be discarded or employed elsewhere or worked up. Furthermore, at a relatively high solids content, the molecular chains are destroyed due to the intensive shearing stresses on the gel, and the desired properties of the product are thus adversely influenced.

DE-A 3519013 describes the preparation of pulverulent, water-soluble polymers by polymerization of water-soluble, ethylenically unsaturated monomers in a powder bed, water-insoluble polymerization initiators being employed in the form of liquid, organic peroxides. In this reaction, the heat of polymerization is removed by evaporation of water, the circulated powder bed being retained.

DE-A 3842184 describes a process in which water-soluble, monoethylenically unsaturated monomers are polymerized to pulverulent hydrophilic polymers in a powder bed. The particle size is controlled in this process by atomizing the solution of the monomers together with an inert auxiliary liquid with the aid of a multi-component nozzle immersed in the bed. The inert stream of atomizing gas regulates the particle size of the polymers by its variation in its amount.

DE-A 3842185 describes a process for the preparation of pulverulent monomers from acrylic and methacrylic acid in a powder bed. The monomers are added in a mixture of water and alcohols with polymerization initiators and regulators, the powder state being maintained, and the reaction mass is circulated mechanically and the heat of reaction removed by distilling off the solvents. Thiocarboxylic acid and/or mercapto alcohol and propionic acid and/or formic acid are employed as regulators in a defined range of amounts in this process.

EP-A 113048 also describes a process for the preparation of pulverulent polymers based on water-soluble ethylenically unsaturated monomers in an agitated powder bed, a tank, stirred autoclave or flow tube being possible as the device. In this process, the monomers are added to the powder bed in mixtures with water or water/isopropanol, this being maintained. The heat of polymerization is removed by distilling off the solvents. 40–95% of the acid groups of the monomers are neutralized here and the polymerization proceeds in the presence of thiocarboxylic acid and further substances as regulators.

The processes according to DE-A 3519013, DE-A 3842185 and EP-A 113048 do not relate to water-swellable polymers and therefore have no relevance with respect to the present invention.

The process according to EP-B 223 063 has the disadvantage that the process proceeds via the gel phase and relatively high solids contents during further processing of the gel lead to difficulties due to the high energy consumption of the apparatus and to a reduction in the properties of the products. Furthermore, the gel particles must be dried, ground and sieved. The undesirable fine particle content must be recycled or discarded, which is undesirable from an economic and ecological aspect.

DE-A 3842184 also relates to the preparation of crosslinked polymers containing acrylic acid. However, no fluidized bed polymerization process is described here, but a process of fixed bed polymerization, i. e. the reaction solution is sprayed onto a mechanically agitated or stirred fixed bed of polymerized particles. An inert diluent, by evaporation of which the heat of polymerization can be removed, must be added here. A temperature of the fixed bed is established according to the evaporation temperature of the inert solvent, i. e. the polymerization temperatures rises to values which are prohibitive for achieving certain properties of the products.

Devices which are mentioned for this process are tanks, stirred autoclaves, combinations of a stirred tank and flow tube or stirred tank cascades, that is to say devices which produce a mechanically agitated powder bed. In contrast, in a fluidized bed, the heat is removed from the polymerized particles dispersed in the fluidizing gas to the gas easily and according to the temperature and amount of fluidizing gas fed in. In this case, the bed temperature can be kept in the range which is more advantageous for the polymerization and the resulting properties via the intake parameters. Furthermore, by dispersing the particles, their sticking together is counteracted far better than in a powder bed densely packed with particles.

The object of the present invention is to provide a process for the preparation of hydrophilic hydrogels of high swelling capacity which does not have the abovementioned disadvantages and in which as far as possible no dust and no fine contents are obtained.

SUMMARY OF THE INVENTION

The present invention therefore relates to a process for the preparation of hydrophilic hydrogels of high swelling capacity by polymerization of hydrophilic (co)monomers, wherein the polymerization is carried out in a fluidized bed apparatus.

The present invention preferably relates to a process for the preparation of hydrophilic hydrogels of high swelling capacity by polymerization of hydrophilic (co)monomers in the presence of water, aqueous alkali and a crosslinking agent, which comprises carrying out the polymerization in a fluidized bed apparatus, wherein the (co)monomers, water, aqueous alkali and crosslinking agent are sprayed into a fluidized bed through multi-component nozzles which are charged with pressurized gas and sprayed from the bottom upward, the multi-component nozzles are immersed in the fluidized bed, the fluidized bed is generated by a hot stream of inert gas which is passed through an inflow tray and granules on the top from the bottom upward, the particles in the fluidized bed are heated by the hot stream of inert gas and as a result the reaction of the (co) monomers and crosslinking agent sprayed onto this is initiated and controlled, and drying of these particles takes place in the fluidized bed, utilizing the heat of polymerization and/or neutralization.

The process according to the invention can be operated both discontinuously and continuously.

BRIEF DESCRIPTION OF THE DRAWING

FIG. 1 is a schematic illustration of an apparatus used in the process of this invention, showing a fluidized bed zone and related feed, product discharge, metering, size selection (sieving), and recycling devices or conduits.

FIG. 2 is a cross-sectional view, greatly enlarged, of a typical form of modified granule produced by the process of this invention.

DETAILED DESCRIPTION

If desired, one or more polymerization initiators can additionally be employed to initiate the polymerization reaction.

The comonomers can be premixed with the aqueous alkali, in particular sodium hydroxide solution or potassium hydroxide solution in a concentration of 30–50%, in a static or dynamic mixer, for example Supraton, directly before the nozzle discharge. However, it is also possible for the two components to be fed separately to the nozzle tip, so that the neutralization takes place only after the nozzle.

If an initiator is employed, this can be fed to the pressurized gas at the nozzle discharge with a metering pump which generates a higher pressure than the inert gas pressure.

The solids content in the reaction mixture can be between 30 and 90% by weight, advantageously between 50 and 70% by weight. Solids contents in aqueous reaction mixtures at which the heat of neutralization and polymerization liberated meets the heat requirement for the noticeable heat and the evaporation enthalpy of the water are particularly favorable. For example, in the case of polymerization of acrylic acid, this range is a solids content of 60–65% by weight.

The degree of neutralization depends on the desired use profile of the granules to be prepared. Customary pH values of the granules are 5.5–6.5.

The process according to the invention can proceed at temperatures in the fluidized bed of 60 to 120° C., preferably between 80 and 105° C. The intake temperature of the fluidizing gas in the bed is essentially determined by the solids content and the heat of neutralization and polymerization, and can be up to 30° C. below and up to 80° C. above the fluidized bed temperature.

By spraying the reaction solution onto particles present at a defined temperature, the solution applied in a very thin layer is reacted very rapidly and granules with an onion-like shell build-up are formed.

The advantage of this procedure is that the tacky and very viscoelastic gel phase, which causes enormous difficulties during processing, especially in the case of gels with a relatively high solids concentration, is avoided here, since drying in the thin layer also takes place simultaneously during the reaction. The reaction in a fluidized bed, i. e. in a stream of gas, in which the particles are dispersed also prevents the particles from being able to stick to the walls. By the formation of an onion-like shell build-up during the reaction, there is furthermore the possibility of producing different properties in the granules by varying the (co) monomers at varying times.

The stream of inert gas for generating the fluidized bed is heated up to the required temperature before entry into the apparatus and adjusted to a throughput of 2,000 to 8,000 $m^3/m^2h$, preferably 5,000 to 7,000 $m^3/m^2h$. The stream of inert gas which leaves the fluidized bed and is loaded with water vapor is freed from entrained fine contents, which in turn fall back into the fluidized bed, in a cyclone or a filter cleaned by pressurized gas.

In the case of monocomponent granules, the process according to the invention can be employed particularly readily in a continuous procedure. Requirements for defined particle distributions of the granules can be met here in a simple manner. In the process according to the invention, the continuous procedure is preferred, which comprises a process in which a) a solution of the reaction components is sprayed into a fluidized bed through multi-component nozzles which are charged with pressurized gas and sprayed from the bottom upward, an initiator, which is employed if appropriate, being fed separately to the nozzle tip and being mixed with the solution in the atomizing cone, this fluidized bed being generated by a hot stream of inert gas which is passed through an inflow tray and granules on top from the bottom upward, and the multi-component nozzles being immersed in the fluidized bed, and b) the reaction of the reaction components sprayed onto the surface of the particles takes place in the fluidized bed in a controlled manner due to the temperature of the stream of inert gas entering, and drying of these particles takes place here in the fluidized bed, utilizing the heat of polymerization and/or neutralization, and c) a stream of granules is removed continuously from the fluidized bed and passed over a sieve, the oversize particles are comminuted on a mill and recycled to the fluidized bed together with the undersized particles separated off at the sieve, correctly sized particles being added to this material to be recycled in a proportion which exceeds the amount of solid fed to the fluidized bed apparatus in the form of the aqueous reaction mixture, and d) the solid is removed via a pipe located centrally or off-center at the base, at the end of which a fluidized bed is generated by a small stream of inert gas fed via an inflow tray from the bottom upward, so that the same circumstances as in the fluidized bed apparatus are established in the discharge pipe and uniform removal via a cellular wheel sluice located on the side of the inflow tray is ensured.

The stream of inert gas loaded with water vapor leaves the fluidized bed apparatus via a cyclone or, more advantageously, via a filter cleaned by pressurized gas. This stream of gas can be recirculated and fed back to the fluidized bed. In this case, the entire stream is fed over a washer condenser, operated under neutral or alkaline conditions, with a subsequent aerosol separator. The amounts of this purified inert gas stream required for the discharge and the compression of the pressurized gas are removed and the remainder is fed, heated to the intake temperature, into the fluidized bed.

If there are strict requirements of the classes of particle size of the granules to be prepared, sieving is carried out with several decks in the sieve, which have mesh widths of the sieve screen corresponding to the desired particle size classes. In this case, the upper deck advantageously determines the upper limit and the lower deck the lower limit of the particle size distribution. The mesh width of the middle decks is then chosen such that a specified particle size class is achieved in the properly sized particles by sluicing out an appropriate amount for each deck fraction. Using metering screws, the particular weight content is removed from the stream of granules leaving the decks and the individual streams are combined to the product stream. The excess properly sized particle classes sieved off is combined and recycled into the fluidized bed apparatus.

The ratio of recirculated amount of material to amount of properly sized particles removed is preferably between 1 and 10.

The granules prepared by the process according to the invention as a rule have particle sizes of 100 $\mu$m to 2 mm, preferably 200 to 800 $\mu$m, particularly preferably between 300 and 600 $\mu$m.

Bi- or multi-component granules can also be prepared by the process according to the invention in a discontinuously proceeding operation, which comprises a process in which
a) material, for example polymerized granules, natural substances, for example starch granules, or inert substances, is initially introduced into the fluidized bed and
b) various reaction mixtures are sprayed on and polymerized successively with respect to time or at varying times.

It is possible, by the process according to the invention, to modify the surface properties of the hydrophilic gels, for example to hydrophobize or hydrophilize them, or to modify the permeability, swelling properties or absorbency and the like by spraying on modifying agents in the fluidized bed after the polymerization reaction.

The modifying agents are as a rule dissolved or emulsified in water or a solvent. The temperature in the fluidized bed is controlled here by the temperature of the stream of inert gas entering the fluidized bed such that the temperature conditions necessary for initiation and progress of the reaction and/or drying of the modifying agent are maintained.

A requirement of the process according to the invention, both in the discontinuous and in the continuous procedure, is initial introduction of granules before the reaction mixture is sprayed in. The particle size distribution of this material is chosen according to application. As a rule, in the case of mono-component granules, a material of the same composition as the product which is to be prepared is initially introduced.

Monomers which are particularly suitable for the process according to the invention are, for example, acrylic acid, methacrylic acid, acrylamidopropanesulfonic acid, vinylphosphonic acid, vinylsulfonic acid, styrenesulfonic acid, crotonic acid, maleic acid, maleic acid half-esters, maleic anhydride, maleic acid half-amides, acrylamides, methacrylamides, vinylpyrrolidones, vinylamides, such as N-vinyl-N-methylacetamide and N-vinylformamide, N-vinylcaprolactam, hydroxyalkyl esters of acrylic or methacrylic acid, vinylpyridines, N,N-dimethyldiallylammonium chloride and aminoalkyl esters and aminoalkylamides of acrylic and methacrylic acid.

These monomers are preferably employed in the form of aqueous solutions. If they are acids, they can be employed in the form of the free acids or in the form of the alkali metal, ammonium or amine salts and mixtures thereof. Mixtures of the monomers mentioned can also be employed in the process according to the invention. Particularly preferred monomers are acrylic acid and methacrylic acid.

Further comonomer components, which can be employed in an amount of up to 30% by weight of the total monomers, are, for example, ($C_1$–$C_{22}$)-esters of acrylic, methacrylic or maleic acid and polyoxyalkylene esters of these acids, vinyl esters, such as vinyl acetate, or versatic acid, as well as polyoxyalkylene esters of these acids, vinyl esters, such as vinyl acetate or versatic acid vinyl ester, styrene, vinyltoluene and acrylonitrile.

Crosslinking agents which can be employed in the process according to the invention are compounds which contain more than one olefinically unsaturated group in the molecule, for example acrylic and methacrylic acid esters of polyhydric alcohols, such as, for example, trimethylolpropane triacrylate and butanediol dimethacrylate, or allyl ethers of polyhydric alcohols, for example neopentylglycol diallyl ether, tetraallyloxyethane, allylamines, such as triallylamine or tetraallylammonium chloride, and divinylbenzene, divinylsulfone, divinyl adipate and N-methylenebisacrylamide.

Polymerization initiators which can be employed in the process according to the invention, if appropriate, are the customary per-compounds, such as dibenzoyl peroxide, tert-butyl hydroperoxide, cumene hydroperoxide, potassium peroxodisulfate, sodium peroxodisulfate and ammonium peroxodisulfate, and azo initiators, such as azoisobutyronitrile. Redox systems, such as, for example, hydrogen peroxide/ascorbic acid, peroxodisulfate/Na pyrosulfite and aldehydesulfoxylates/peroxides, are preferably employed.

Suitable modifying components for the process according to the invention are liquid substances, such as, for example, polyalkylene oxides, in particular polyethylene glycols, polypropylene glycols and polyglycols having a molecular weight of up to about 600, paraffins, polyamines, such as, for example, ethylenediamine and diethylenetriamine, polyethyleneimine, polyglycidyl compounds, such as, for example, ethylene glycol diglycidyl ether, propylene glycoldiglycidyl ether, polyethylene glycol diglycidyl ether and glycerol polyglycidyl ether, liquid polyhydric alcohols, such as, for example, glycerol, pentaerythritol, trimethylolpropane, neopentyl alcohol, sorbitol and polyvinyl alcohol, and solutions of poly(meth)acrylates, polyamidoamines, polyvinyl acetate and copolymers.

Diglycidyl compounds, polyglycidyl compounds and polyamines, for example ethylene glycol diglycidyl ether, polyethylene glycol diglycidyl ether, diethylenetriamine and polyethyleneimine, are particularly preferred.

In the process according to the invention, modifying components are bonded absorptively to the surface if they contain no groupings incorporated in the molecule which react chemically with the surface of the hydrogen particles. Modifying components which contain groupings which are capable of reacting chemically with the surface of the hydrogel particles can form covalent, ionic or complex bonds, such as, for example, polyglycidyl compounds, polyanions, polycations or polyvalent metal cations.

Turning now to the Drawing, FIG. 1 illustrates substantially the complete apparatus 10 utilized in the process of this invention, including the fluidized bed reactor or zone 12 and the related feed, product discharge, metering, size selection (sieving), and recycling devices or conduits. The fluidized bed 14 is generated above the inflow tray (distribution plate or grid) 18 by introducing granules through a suitable feeding device 16, which is in communication with the region of fluidized bed zone 12 above the inflow tray 18, and by passing heated inert gas (introduced at 20) through the inflow tray 18 and the granules inside fluidized bed zone 12, thereby elevating the mass of granules to form the fluidized bed 14.

A solution of reactants 22 is introduced my a metering pump 27 over the pressure provided by a pressurized gas and is sprayed onto the granules in fluidized bed 14 through multi-component nozzles, which are in the form of atomizer cones 24, cones 24 being fed by manifold 26. The initiator is introduced separately with the aid of metering pump 28 (and through its own separate manifold 30), but the initiator is also sprayed through the atomizer cones 24.

The hot inert gas effluent (which includes water vapor from the spray emanating from atomizer cones 24) passes through a filter 34(cleaned by pressurized gas) and outlet 32 to a recovery system which includes a washer and condenser unit 36 and an aerosol separator 37.

Solids are removed from the fluidized bed 14 via a pipe 38 at the base of zone 12 and fed to a second fluidized bed 114, similarly generated above a second inflow tray 118 with the aid of a relatively smaller inert gas flow passed upward through inflow tray 118. This use of a second fluidized bed 114 insures trouble-free removal of granules through sluice 119.

This stream of granules 121 is continuously removed from fluidized bed 14 and is passed by a pneumatic conveyor 122 to a sieve 44 having a plurality of screens or decks 46, so that fines and oversize particles can be dealt with without detracting from the overall efficiency of the process. (Pneumatic conveyor pressure can be bled or released through filter 45.) Oversize particles are flowing to a mill 50, so that they can be reduced to the proper size and recycled via granule reservoir 52 and conduit 54 through feeding device 16 to the fluidized bed 14, together with undersized particles flowing from sieve 44. Correctly-sized particles from the middle of sieve 44 are flowing to reservoir 55 from which the product is removed by a metering device 57. The proportion which exceeds the amount of solid fed to the fluidized bed zone 12 in the form of the aqueous reaction mixture, i.e. solution 22 is the overflow 56 of reservoir 55 and comes back to the fluid bed reactor via 52, 54 and 16.

In a preferred embodiment, sluice 119 is a cellular wheel sluice.

FIG. 2 illustrates a typical form of modified granule 60 resulting from the spraying of solution 22 and initiator onto the surfaces of the granules fluidized in fluidized bed 14. Because of the temperature in fluidized bed 14, at least one very thin layer of hydrophilic polymer of high swelling capacity forms very rapidly on granule 60 and is simultaneously dried in situ utilizing the heat of polymerization and/or neutralization. An onion-like shell 62 builds up on granule 60, and, if desired, the granular product 60 can be further modified with spray treatments after the polymerization reaction.

What is claimed is:

1. A process for the preparation of granules, which are surface-modified with water-swellable, hydrophilic polymer in a fluidized bed zone having nozzles immersed therein and containing the granules, and at least one polymerizable hydrophilic polymer-forming monomer, said process comprising:

introducing granules into the fluidized bed zone and generating a fluidized bed comprising granules by passing upwardly into the fluidized bed zone a gas flow, which is heated while in said fluidized bed zone, the gas of said gas flow being inert toward the granules and the hydrophilic polymer-forming monomer at the temperature of the fluidized bed, spraying through said nozzles upwardly onto the granules, in the fluidized bed, an aqueous medium and a said hydrophilic polymer-forming monomer and forming on granules thus sprayed a layer containing the aqueous medium and the hydrophilic polymer-forming monomer, heating the granules in the fluidized bed with the heated gas flow, and with polymerization taking place on the surface of the granules, said heating being sufficient to dry the granules sprayed with the aqueous medium, and recovering from said fluidized bed zone granules which have applied thereto a shell comprising water-swellable, hydrophilic polymer.

2. The process as claimed in claim 1, wherein the granules recovered from the fluidized bed zone, which granules have applied thereto a shell comprising water-swellable, hydrophilic polymer, have a particle size in the range of about 100 micrometers to about 2 millimeters.

3. The process as claimed in claim 1 or 2, which is carried out continuously, wherein a) a solution of the reaction components is sprayed into a fluidized bed through multi-component nozzles which are charged with pressurized gas and sprayed from the bottom upward, an initiator, which is optionally employed, being fed separately to the nozzle tip and being mixed with the solution in an atomizing cone, this fluidized bed being generated by a hot stream of inert gas which is passed through an inflow tray and granules on top from the bottom upward, and the multi-component nozzles being immersed in the fluidized bed, and b) the reaction of the components sprayed onto the surface of the particles takes place in the fluidized bed in a controlled manner due to the temperature of the stream of inert gas entering, and drying of these particles takes place in the fluidized bed, utilizing the heat of polymerization and/or neutralization, and c) a stream of granules is removed continuously from the fluidized bed and passed over a sieve oversize particles are comminuted on a mill and recycled to the fluidized bed together, with undersized particles separated off at the sieve, correctly sized particles being added to this material to be recycled in a proportion which exceeds the amount of solid fed to the fluidized bed apparatus in the form of the aqueous reaction mixture, and d) the solid is removed via a pipe located centrally or off-center at the base, at the end of which a fluidized bed is generated by a small stream of inert gas fed via an inflow tray from the bottom upward, so that the same conditions as in the fluidized bed apparatus are established in the discharge pipe and uniform removal via a cellular wheel sluice located on the side of the inflow tray is ensured.

4. The process as claimed in claim 1, wherein the surface properties of the hydrophilic water-swellable polymer are modified by spraying on modifying agents in the fluidized bed after polymerization reaction.

5. The process as claimed in claim 1, wherein the monomers or comonomers are selcted from the group consisting of acrylic acid, methacrylic acid, acrylamidopropanesulfonic acid, vinylphosphonic acid, vinylsulfonic acid, styrenesulfonic acid, crotonic acid, maleic acid, maleic acid half-esters, maleic anhydride, maleic acid half-amides, acrylamides, methacrylamides, vinylpyrrolidones, vinylamides, such as N-vinyl-N methylacetamide and N-vinylformamide, N-vinylcaprolactam, hydroxyalkyl esters of acrylic or methacrylic acid, vinylpyridines, N.N-dimethyl-diallylammonium chloride or aminoalkyl esters or aminoalkylamides of acrylic and methacrylic acid.

6. The process as claimed in claim 4, wherein a modifying agent sprayed in the fluidized bed is selected from the group consisting of a paraffin, a polyamine, a polyglycidyl compound, a liquid polyhydric alcohol, a solution comprising a polyacrylate, a polymethacrylate, a polyadmidoamine, polyvinyl acetate, or a copolymer thereof, a polyglycol having a molecular weight up to about 600 and a liquid polyalkylene oxide.

7. The process as claimed in claim 1, wherein the fluidized bed zone contains an inflow tray, the granules are introduced into the fluidized bed zone at a position above the inflow tray, and heated gas flow is passed upwardly through the inflow tray.

8. The process as claimed in claim 1, wherein the aqueous medium is an aqueous alkaline medium, the granules or the hydrophilic polymer-forming monomer are acidic, or both the granules and the polymer-forming monomer are acidic, and the aqueous alkaline medium undergoes a heat-producing neutralization reaction with the granules or the hydrophilic polymer-forming monomer.

9. The process as claimed in claim 1, wherein an initiator or a crosslinking agent or both an initiator and a crosslinking agent are sprayed upwardly into the fluidized bed zone onto the granules, and the resulting polymerization reaction generates heat which assists in drying the granules while the granules are in the fluidized bed.

10. The process as claimed in claim 1, wherein the granules, as introduced into the fluidized bed zone, comprise a solid hydrophilic polymer.

11. The process as claimed in claim 2, wherein a granule stream is removed from the fluidized bed zone, said granule stream including granules within the said particle size range and undersize and oversize granules, wherein the oversize granules are milled to be within the said particles size range, and wherein the undersize granules are recycled to the fluidized bed zone.

12. The process as claimed in claim 1, wherein the properties of the granules, while in the fluidized bed zone but after said chemical reaction has taken place on the surfaces of the granules, are further modified by spraying a modifying agent onto the surfaces of the granules.

13. The process as claimed in claim 1, wherein said gas flow is heated prior to being passed upwardly into said fluidized bed zone.

14. The process as claimed in claim 13, wherein the gas flow through said fluidized bed zone flows upwardly through said zone at a throughput rate of 2,000 to 8,000 $m^3/m^2/h$.

* * * * *

UNITED STATES PATENT AND TRADEMARK OFFICE
CERTIFICATE OF CORRECTION

PATENT NO. : 6,150,477
DATED : November 21, 2000
INVENTOR(S) : Fritz Engelhardt, Manfred Mayer, and Uwe Nickel It is certified that error appears in the above-identified patent and that said Letters Patent is hereby corrected as shown below:

Column 8,
Line 32, (claim 3, line 6), delete the word "optionally".

Signed and Sealed this

Twenty-third Day of October, 2001

Attest:

NICHOLAS P. GODICI
Attesting Officer  Acting Director of the United States Patent and Trademark Office